US00PP22131P2

(12) United States Plant Patent
Probst

(10) Patent No.: US PP22,131 P2
(45) Date of Patent: Sep. 6, 2011

(54) ***COREOPSIS* PLANT NAMED 'MAMBO'**

(50) Latin Name: ***Coreopsis* hybrid**
Varietal Denomination: Mambo

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/660,454

(22) Filed: Feb. 26, 2010

(51) Int. Cl.
*A01H 5/00* (2006.01)

(52) U.S. Cl. ..... Plt./417

(58) Field of Classification Search ..... Plt./417
See application file for complete search history.

(56) References Cited

U.S. PATENT DOCUMENTS

PP12,720 P2 * 6/2002 Leonard ..... Plt./417

OTHER PUBLICATIONS

Ball Seed for *Coreopsis* 'Sweet Dreams' 2011, retrieved on Mar. 23, 2011. Retrieved from the Internet at <http://www.parkseed.com/gardening/PD/40903/> 2pp.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Mambo' characterized by its inflorescences with ray florets that open creamy white in color with a burgundy eye zone with the creamy white portion aging in a few days to a rose-pink color, its bushy and relatively short plant habit, its floriferous and long blooming habit, its relative sterility, and its vigorous growth habit.

2 Drawing Sheets

Botanical classification: *Coreopsis* hybrid.
Variety denomination: 'Mambo'.

CROSS REFERENCE TO A RELATED APPLICATION

This application is co-pending with a U.S. Plant Patent application filed for a plant derived from similar parentage in the Inventor's breeding program that is entitled *Coreopsis* Plant Named 'Caliente' (U.S. Plant Pat. No. 21,869), *Coreopsis* Plant Named 'Salsa' (U.S. Plant patent application Ser. No. 12/660,464), *Coreopsis* Plant Named 'Limbo' (U.S. Plant patent application Ser No. 12/660,455), *Coreopsis* Plant Named 'Jive' (U.S. Plant patent application Ser. No. 12/660,491), *Coreopsis* Plant Named 'Cha Cha Cha' (U.S. Plant patent application Ser. No. 12/660,480).

BACKGROUND OF THE INVENTION

The present invention relates to a new and distinct cultivar of *Coreopsis* plant, botanically of hybrid origin and known as *Coreopsis* 'Mambo' and will be referred to hereinafter by its cultivar name, 'Mambo'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The Inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique flower colorations, short and bushy plant habits, and sterility to lengthen bloom periods.

The Inventor made a controlled cross in August 2006 in his test garden in Hubbardston, Mass. between an unnamed F6 generation seedling produced from crosses of *Coreopsis tinctoria* and *Coreopsis rosea* as the female parent and an unnamed F6 generation seedling produced from crosses of unnamed hybrid *Coreopsis* from his breeding program and *Coreopsis rosea* as the male parent. 'Mambo' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Mambo' as unique from all *Coreopsis* cultivars known to the Inventor.

1. 'Mambo' exhibits composite inflorescences with ray florets that open creamy white in color with a burgundy eye zone with the creamy white portion aging in a few days to a rose-pink color.
2. 'Mambo' exhibits a bushy plant habit and is relatively short in height; reaching 16 to 24 inches (4.0 to 61 cm) in height.
3. 'Mambo' exhibits a vigorous growth habit.
4. 'Mambo' exhibits a long blooming period with an abundance of blooms; blooming from June through August in Massachusetts.
5. 'Mambo' is relatively sterile and produces very few seeds if any.

The female parent differs from 'Mambo' in having a shorter plant height (reaching 8 to 12 inches in height), in having inflorescences with ray florets that are white in color with a small burgundy eye, and in producing an abundance of seed that shortens its bloom season to one month. The male parent differs from 'Mambo' in being less floriferous and in having inflorescences with ray florets that are solid gold in color. 'Mambo' can be most closely compared to cultivars 'Sweet Dreams' and 'Limerock Ruby' (U.S. Plant Pat. No. 15,455). 'Sweet Dreams', differs from 'Mambo' in being a perennial rather than an annual, in being taller in height when left un-pinched (it is typically pinched in commercial production for height control), in having ray florets that are less overlapping and in having inflorescences that do not differ as much in coloration from a freshly open inflorescence to a three day-old inflorescence. 'Limerock Ruby' differs from 'Mambo' in having inflorescences with ray florets that are solid crimson red in color.

BRIEF DESCRIPTION OF THE DRAWING

The accompanying colored photographs illustrate the overall appearance and distinct characteristics of the new *Coreopsis*. The photographs in the figures were taken in late summer of a six month-old plant of 'Mambo' as grown outdoors in a 2-gallon container in The Netherlands.

The photograph in FIG. 1 shows the floriferous blooming habit of 'Mambo'.

Figure 1:
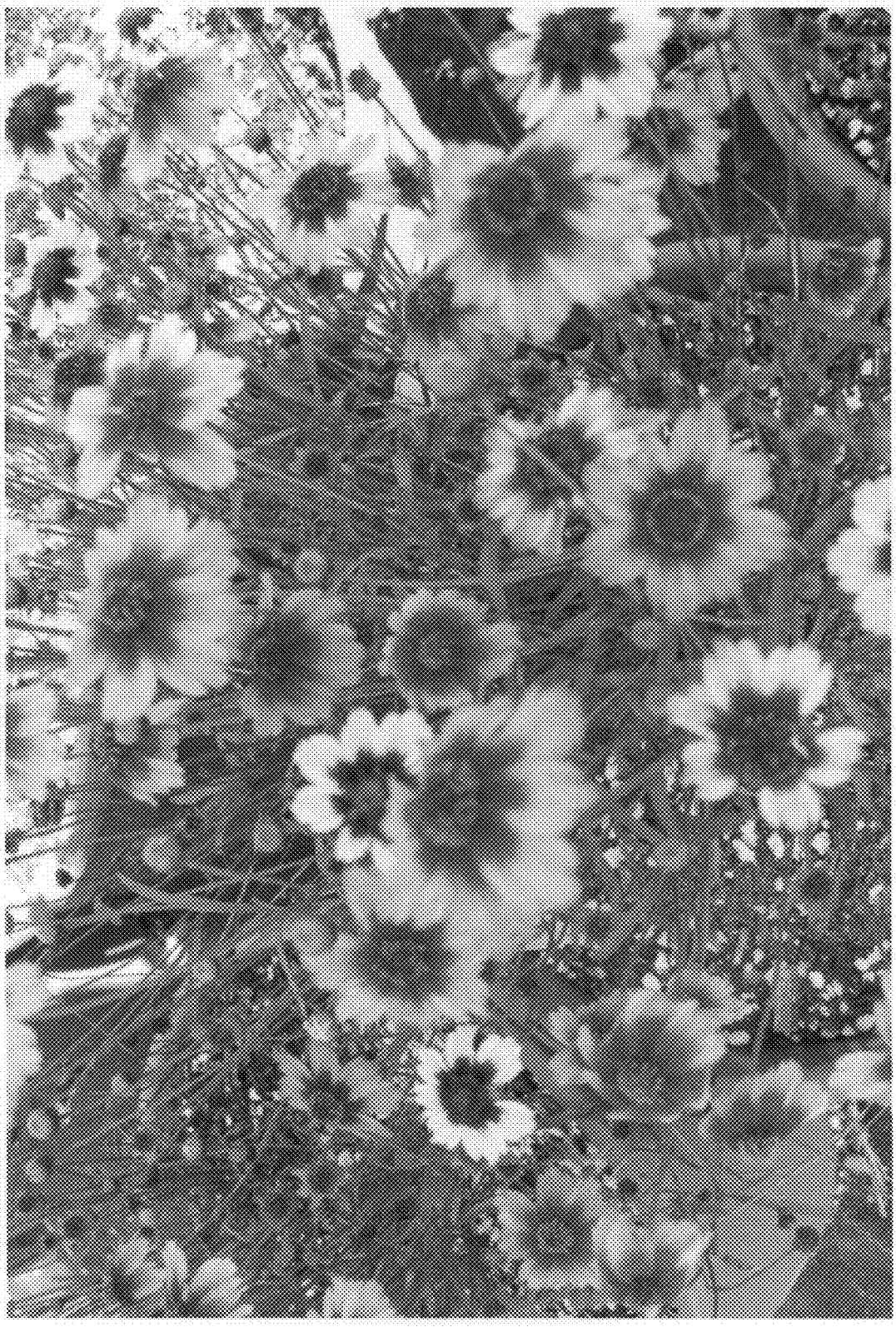
Figure 2:
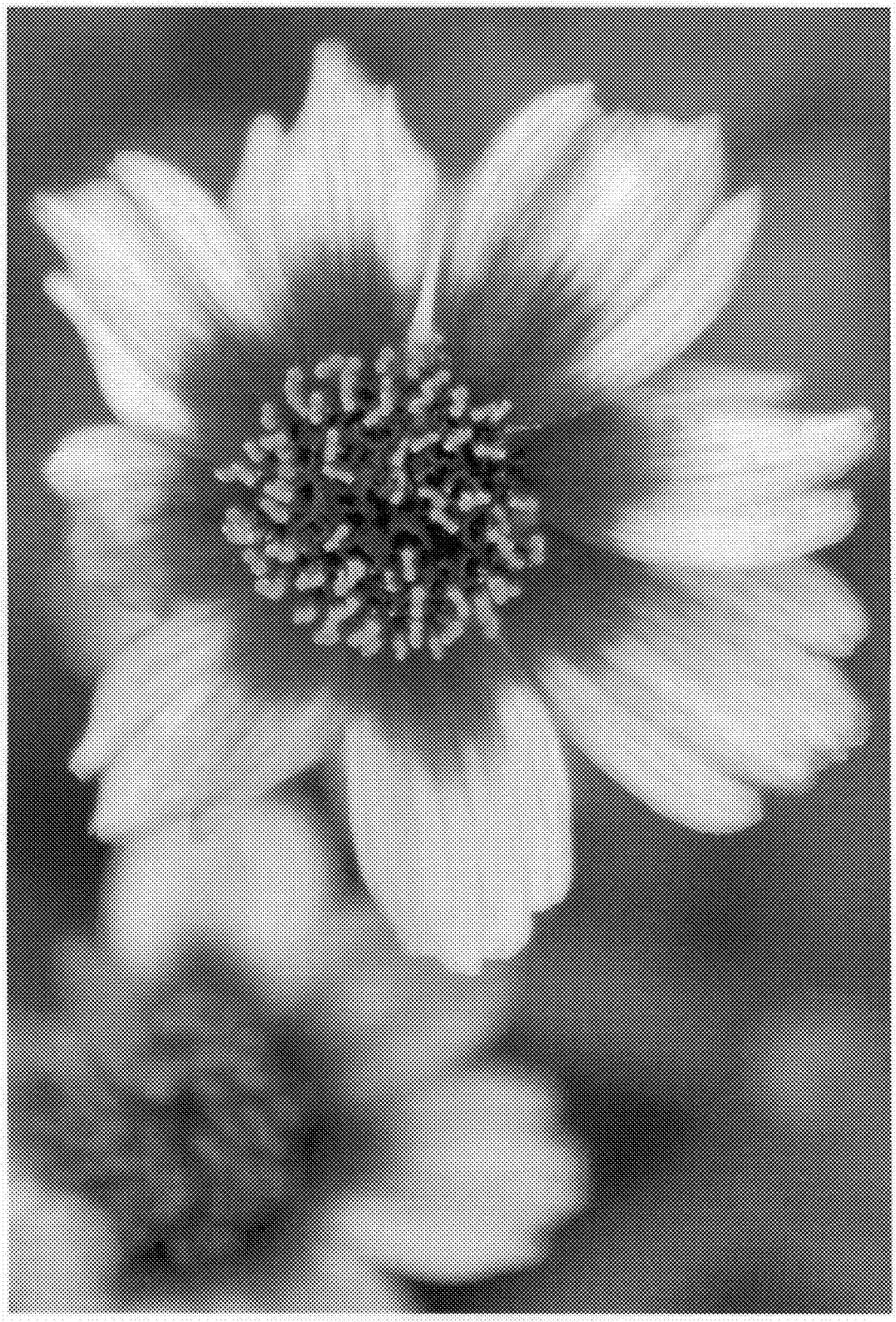

The photograph in FIG. 2 provides a close-up view of inflorescences of 'Mambo'.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June through August in central Massachusetts.

*Plant habit.*—Herbaceous annual, well-branched to produce a bushy habit.

*Height and spread.*—Reaches 16 to 24 inches (40 to 61 cm) in height and about 18 inches (46 cm) in width in 3 months from a rooted cutting.

*Cold hardiness.*—Has not been tested as it is grown as an annual.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous.

Stem description:

*Shape.*—Oval, solid.

*Stem color.*—144A.

*Stem size.*—Main stem averages 33 cm in length with 4 mm in width, laterals an average of 23 cm in length (excluding peduncles), an average of 3 mm in width and tertiary branches about 16 cm in length and 2 mm in width.

*Stem surface.*—Very finely puberulent with some ridges.

*Branching habit.*—An average of 4 basal branches with an average of 6 lateral branches, and 3 terminal flowering branches on each lateral, branch internode length is variable but typically about 5 cm.

Foliage description:

*Leaf division.*—Simple.

*Leaf margins.*—Tri-lobed, entire or five-lobed.

*Leaf size.*—Up to 10.5 cm in length and 10 cm in width when five-lobed with side lobes 4 cm in length and 6 mm in width.

*Leaf shape.*—Fan shaped overall when tri-lobed, ovate in shape when five-lobed, with lobes narrowly lanceolate to linear.

*Leaf base.*—Attenuate.

*Leaf apex.*—Acute.

*Leaf venation.*—Pinnate, not prominent, vein color matches leaf color.

*Leaf attachment.*—Sessile.

*Leaf arrangement.*—Opposite.

*Leaf internode length.*—Variable, an average of 7 cm.

*Leaf quantity.*—An average of 10 per lateral stem.

*Leaf surface.*—Dull and very finely puberulent on upper surface and lower surface.

*Leaf color.*—Young and mature upper surface; 137B, young and mature lower surface; 137C.

Inflorescence description:

*Inflorescence type.*—Composite with ray florets surrounding disk florets in the center forming a radiant head, inflorescences are borne singular to group of 3 at terminal of lateral branches.

*Lastingness of inflorescence.*—About one week until senescence of ray florets, bracts and disk florets are persistent.

*Fragrance.*—None detected.

*Quantity of inflorescences.*—An average of 25 per lateral branch.

*Inflorescence size.*—Average 7 mm in depth and up to 2.6 cm in diameter with disk portion an average of 8 mm in diameter.

*Inflorescence buds.*—Average of 5 mm in depth and 5 mm in diameter, shape is spherical, color is a blend of 167B and 147A, with bracts 137B.

*Peduncle.*—Average of 9 cm in length and 1 mm in diameter, 137B in color, finely puberulent surface.

Involucral bracts:

*Bract number.*—Three rows, one row of outer bracts with an average of 7 and two rows of inner bracts with an average of 4.

*Bract arrangement.*—Outer bracts are un-fused spreading and slightly cupped upward, inner bracts overlap and surround receptacle with a campanulate form with apical portion un-fused, spreading, and held close to ray florets.

*Bract size.*—Outer bracts about 2.5 mm in length and 1.5 mm in width, inner bracts about 6 mm in length and 2.5 mm in width with free portion an average of 3 mm in length and 2.5 mm in width.

*Bract color.*—Outer bracts 137B in both surfaces, inner bracts; fused portion 147A, un-fused portion is a blend of 25A and 147A.

*Bract texture.*—Outer bract; puberulent, waxy, inner bracts glabrous and waxy.

*Bract apex.*—Outer bract; acute, inner bracts; acute.

*Bract base.*—Truncate.

*Bract shape.*—Outer bracts; broadly lanceolate, inner bracts; free portion broadly ovate.

Ray florets (sterile):

*Number.*—8.

*Shape.*—Elliptic.

*Size.*—Average of 1.2 cm in length and 8 mm in width.

*Apex.*—Truncate with notches.

*Base.*—Broadly cuneate.

*Margins.*—Entire on sides, notched with 3 to 4 notches at apex.

*Aspect.*—Held nearly horizontal.

*Surface.*—Glabrous on both surfaces.

*Color.*—Upper surface when newly opened; a blend of 1B and 1D with eye zone 59A, when fully open (in a few days); a blend of 1C and 1D and suffused with 59B for a rose-pink appearance with an eye zone of 59B, lower surface when opening and fully open; 150A and 150C with eye zone N77A.

Disk florets (male and female):

*Shape.*—Tubular, corolla is fused, flared at apex.

*Size.*—About 6 mm in length and 1 mm in width.

*Color.*—In masse; when fully open N77A with tips 17A, corolla; base (tube) is 8B, flared portion is N79B and translucent.

*Receptacle.*—About 3.5 mm in diameter and 1 mm in depth, 146D in color.

Reproductive organs:

*Presence.*—Disk florets are perfect, ray florets are sterile.

*Gynoecium.*—1 Pistil, 5 mm in length, style is very fine and about 160A in color and translucent, bifid pilose stigma is 17A in color with branches about 1 mm in length and recurved, ovary is 2 mm in length, 1 mm in width, inferior, and 157C in color.

*Androcoecium.*—5 stamens, fused into tube surrounding style, 2 mm in length and 0.4 mm in width, about 200A in color, no pollen was observed.

*Fruit/seed.*—Relatively sterile and produces very few seeds if any.

It is claimed:

1. A new and distinct cultivar of *Coreopsis* plant named 'Mambo' as herein illustrated and described.

* * * * *